United States Patent [19]

Beiter et al.

[11] 4,191,580

[45] Mar. 4, 1980

[54] STABLE DISPERSIONS CONTAINING TRIALKYLTIN FLUORIDES

[75] Inventors: Charles B. Beiter, Carteret; Leroy A. Hafner, Edison, both of N.J.

[73] Assignee: M&T Chemicals Inc., Woodbridge, N.J.

[21] Appl. No.: 874,232

[22] Filed: Feb. 1, 1978

Related U.S. Application Data

[63] Continuation-in-part of Ser. No. 763,406, Jan. 28, 1977, Pat. No. 4,153,574.

[51] Int. Cl.$^2$ .............................................. C09D 5/14
[52] U.S. Cl. ................................... 106/16; 106/18.36; 106/237; 106/239; 106/241; 260/33.4 R; 260/33.6 A; 260/33.6 UA; 260/42; 424/288
[58] Field of Search ..................... 106/15 R, 237, 239, 106/241, 16, 18.36; 424/288; 260/33.4 R, 33.6 A, 33.6 UA, 42

[56] References Cited

U.S. PATENT DOCUMENTS

| | | | |
|---|---|---|---|
| 3,214,279 | 10/1965 | Scott | 106/15 R |
| 4,012,503 | 3/1977 | Freiman | 106/15 R |

Primary Examiner—Lorenzo B. Hayes
Attorney, Agent, or Firm—Kenneth G. Wheeless; Robert Spector

[57] ABSTRACT

The tendency of dispersions containing trialkyltin fluorides in organic liquids to agglomerate is avoided by using as the dispersion medium specified organic liquids in combination with from 0.5 to 10%, based on the weight of the dispersion, of specified inorganic compounds. The choice of both organic liquid and inorganic compounds is critical to achieving long-term stability of the resultant dispersion.

8 Claims, No Drawings

STABLE DISPERSIONS CONTAINING TRIALKYLTIN FLUORIDES

FIELD OF THE INVENTION

This application is a continuation-in-part of application Ser. No. 763,406, filed on Jan. 28, 1977 U.S. Pat. No. 4,153,574.

This invention relates to compositions containing a dispersed form of a trialkyltin fluoride. More particularly, this invention relates to stable dispersions of trialkyltin fluorides which are capable of being stored for extended periods of time without any significant increase in viscosity.

A number of trialkyltin fluorides, particularly tri-n-butyltin fluoride, effectively inhibit the attachment and growth of barnacles and other organisms responsible for fouling of submerged surfaces such as the hulls of sea-going vessels and the pilings of docks and other facilities exposed to salt water. The trialkyltin fluorides are, therefore, useful as the toxicant for antifouling coatings. A typical antifouling coating contains the toxicant, one or more pigments and a film-forming polymer. All of these components are dissolved or dispersed in an organic solvent such as xylene or toluene, optionally in combination with a ketone such as 2-butanone.

Up until now, acceptable coatings containing trialkyltin fluorides, which are solid materials at ambient temperatures, have been difficult to prepare. Dispersions of trialkyltin fluorides in organic solvents exhibit a strong tendency to agglomerate in the form of large particles. These materials therefore cannot be dispersed in coating compositions or organic solvents by mixing at high speeds. This unusual behavior can be explained in terms of a difference between the electronegativities of tin and fluoride. This difference results in a relatively weak attractive force between the tin atom on one molecule and the fluoride atom on an adjacent molecule, resulting in a structure resembling that of a linear polymer molecule. Regardless of the cause, the agglomeration is undesirable, since it makes it difficult or impossible to prepare a useful coating formulation wherein the maximum particle size is 45 microns or less. This degree of fineness cannot be achieved without grinding the formulation in a pebble mill or a ball mill, a tedious, time-consuming operation. Even following such a grinding procedure, there may still be a number of hard agglomerates present in the formulation. These agglomerates must be removed manually to obtain a useful coating composition.

It is, therefore, an objective of this invention to obtain stable dispersions of trialkyltin fluorides which can be readily dispersed in coating compositions without the need for grinding to achieve the desired particle size.

Surprisingly, it has now been found that the presence of certain inorganic compounds enable trialkyltin fluorides such as tri-n-butyltin fluoride to be dispersed in a specified class of organic solvents without agglomeration to yield stable compositions. The resultant compositions remain stable for extended periods of time and can readily be incorporated into coating compositions, including paints.

Japanese Patent Publication No. 7338847 discloses heating tri-n-butyltin fluoride at 40° to 60° C. in a liquid hydrocarbon or halogenated hydrocarbon that boils from 50° to 200° C. The resultant slurry hardens upon standing for any appreciable length of time, and hence is not practical for incorporation into antifouling coatings. Even after being ground the resultant particles do not yield a dispersion of adequate "fineness".

SUMMARY OF THE INVENTION

This invention provides a stable, thixotropic dispersion of a trialkyltin fluoride, said dispersion consisting essentially of:

(1) from 40 to 70% by weight of a trialkyltin fluoride of the formula $R_3SnF$, wherein R is alkyl containing from 2 to 12 carbon atoms;

(2) from 20 to 60% by weight of at least one organic liquid having a kauri butanol value of 96 or less and selected from the group consisting of alcohols containing from 4 to 12 carbon atoms, aliphatic hydrocarbons containing from 5 to 12 carbon atoms, aromatic hydrocarbons;

(3) from 0.5 to 10% by weight of a compound selected from the group consisting of:
 (a) lithium and sodium salts of p-toluenesulfonic, phenylphosphonic and silicic acids;
 (b) nitric acid salts of calcium, magnesium, sodium, lithium, iron and zinc;
 (c) salts of p-toluenesulfonic or phenylphosphonic acid and an element selected from the group consisting of magnesium, calcium, strontium and barium;
 (d) the chlorides of metallic elements selected from the group consisting of divalent copper, silver, gold and the elements in Groups II-A, II-B, IV-A, IV-B, V-A, VI-B, VII-B and VIII of the periodic table, and
 (e) carboxylic acid salts of lead, manganese, zirconium, barium and strontium, wherein said carboxylic acid contains from 2 to 12 carbon atoms.

DETAILED DESCRIPTION OF THE INVENTION

The novel feature of the present trialkyltin fluoride compositions resides in the presence, in relatively small amounts, of compounds derived from one of the metallic elements. These compounds stabilize the dispersion by preventing agglomeration of the trialkyltin fluoride particles. The accompanying examples demonstrate that many members of this class of compounds are not suitable stabilizers, and it is therefore difficult to predict without experimentation which compounds are operable. For example, while sodium compounds are generally useful, the only effective potassium compound is the hydroxide. The liquid medium is also a critical factor with respect to stability of the dispersion.

The cationic portion of those compounds found to be effective dispersion stabilizers is derived from one of a number of specified metallic elements, and includes members from groups I-A, I-B, II-A, II-B, IV-A, IV-B, V-A, VI-B, VII-B and VIII of the periodic table. The anionic portion of the molecule is a residue of an inorganic acid such as nitric or silicic acid, or an organic acid such as p-toluenesulfonic acid, phenylphosphonic acid or a carboxylic acid containing from 2 to 12 carbon atoms. Representative carboxylic acids include acetic, propionic, butyric, hexoic, heptanoic, cyclohexanecarboxylic and benzoic acids.

Chlorides of polyvalent metallic elements are also effective dispersion stabilizers. By comparison, a dispersion containing sodium chloride solidifies upon standing. With the exception of potassium hydroxide, this is also true for dispersions containing the potassium analogs of the sodium compounds disclosed in this application and in copending application Ser. No. 763,406, of which the present application is a continuation-in-part.

In addition to choice of the proper inorganic dispersion stabilizer, the organic liquid used as a dispersion vehicle is also critical to obtaining a non-coagulating dispersion of a trialkyltin fluoride. Suitable organic liquids include aliphatic hydrocarbons and aromatic hydrocarbons having a kauri butanol value of 96 or less. The kauri butanol value of a hydrocarbon solvent is equal to the volume in cubic centimeters (measured to 25° C.) of a given solvent that will produce a specified degree of turbidity when added to 20 g of a standard solution of kauri resin in normal butanol. The test method is published by the American Society for Testing and Materials as ASTM Test No. 01133-61 (reapproved in 1973). The pertinent portions of this testing procedure are hereby incorporated by reference.

Representative useful liquid hydrocarbons include the aliphatic hydrocarbons. These hydrocarbons can be used individually or in mixtures that are commercially available as mineral spirits, petroleum ether and naphtha. The class of aromatic hydrocarbons includes xylene. Toluene has a kauri butanol value of 105, and is therefore not a suitable medium for the present dispersions, however, it can be used in mixtures with aliphatic hydrocarbons. Other useful liquid media include alcohols containing 1, 2 or 4 carbon atoms, such as methanol, ethanol and butanol. Surprisingly, a stable dispersion cannot be prepared in n-propanol.

The trialkyltin fluorides that can be employed in the stable dispersions of this invention are of the general formula $R_3SnF$, wherein R is alkyl and contains from 3 to 6 carbon atoms. If the dispersion is to be incorporated into a coating material intended to inhibit fouling by barnacles and other organisms on ship hulls and other normally submerged structures, R is preferably n-butyl.

Using the dispersion stabilizers and organic liquids disclosed in the preceding specification and accompanying claims, it is possible to prepare compositions containing from about 10% up to about 70% by weight of a trialkyltin fluoride. It has heretofore not been possible to incorporate more than about 40% by weight of a trialkyltin fluoride such as tri-n-butyltin fluoride in a dispersion. The maximum amount of fluoride that can be dispersed will, of course, be dependent upon the particular dispersion stabilizer and organic liquid selected.

The physical forms of the present dispersions vary from viscous liquids to semi-solid pastes, depending upon the concentration of the trialkyltin fluoride. One important advantage of these compositions is that they exhibit thixotropy, and can therefore be easily blended by stirring the composition together with other ingredients conventionally used in paints and other coating compositions. These additional ingredients include natural or synthetic film-forming polymers such as rosin and copolymers of vinyl chloride with one or more ethylenically unsaturated monomers such as vinyl acetate, pigments such as titanium dioxide and iron oxide, viscosity modifiers, particularly clays such as bentonite, and one or more organic solvents.

Typical antifouling coatings that can be prepared using the present dispersed form of trialkyltin fluoride contain from 1.0 to 20.0 of the trialkyltin flouride composition, including one or more of the aforementioned salts and organic liquids, from 10 to 50% by weight of pigments, typically titanium oxide or zinc oxide alone or in combination with colored pigments such as ferric oxide, from 10 to 50% by weight of at least one film-forming component, which typically includes vinyl chloride homopolymers and copolymers, rosin and chlorinated rubbers such as polychloroprene, and from 20 to 60% by weight of one or more organic solvents, including xylene, cyclohexanone, 2-butanone and mixtures of hydrocarbons commonly referred to as "aliphatic naphtha" and "high flash naphtha". A small amount of a viscosity modifier such as a bentonite clay is usually included to impart thixotropy to the final coating composition.

The preparation of a particularly preferred coating formulation is described in one of the accompanying examples.

Incorporating tri-n-butyltin fluoride into a paint formulation has heretofore been a lengthy, time-consuming procedure due to the tendency of the flouride to agglomerate. The resultant paint usually must be ground for several hours in a pebble or sand mill to obtain a fineness of 4 to 5 on the Hegman N.S. Scale of 0 (no grind) to 10 (excellent grind). A rating of 4 to 5 on this scale is equivalent to an average particle size of from 40 to 70 microns. Similar problems resulting from agglomeration are encountered if an attempt is made to disperse the trialkyltin fluoride in an organic solvent prior to incorporating it into a paint formulation. In addition, once a dispersion of the desired particle size is obtained, it cannot be stored for any length of time, since it rapidly hardens to a waxy solid.

The accompanying examples disclose preferred embodiments of the present compositions and should not be interpretted as limiting the scope of the accompanying claims. In the examples all parts and percentages are by weight unless otherwise indicated.

EXAMPLE 1

Dispersions of tri-n-butyltin flouride were prepared by blending 60 parts of this compound, 5 parts of the inorganic stabilizer and 35 parts of a mixture containing 64% special naphthalite (a mixture of liquid hydrocarbons containing less than 8% of aromatic hydrocarbons), 12% ethyl benzene, 9% n-butyl acetate, 5% isobutyl acetate and 10% n-butanol. The flash point of the mixture is 14.4° C., the kauri butanol number is 36 and the boiling range is from 123° to 145° C. One hundred grams of the resultant mixture were placed in a cylindrical container measuring two inches (5.1 cm) in diameter and 4.5 inches (11.4 cm) in height. Into the same container were also placed 250 grams of stainless steel spheres measuring 4.7 millimeters in diameter. The container was then sealed and shaken vigorously for twenty minutes, after which the contents of the container were emptied onto a large mesh wire screen. Dispersions which solidified during milling and crumbled when prodded with a spatula were considered unacceptable and were not tested further. Acceptable materials were either viscous liquids or homogeneous, coherent semi-solids which could be forced through the openings of the screen using a spatula. Those materials which passed through the screen were collected and maintained under ambient conditions for two days. At the end of the period, they were examined to determine whether any changes in their physical form had ocurred during this interval. Those materials which had solidified and could no longer be stirred with a spatula were considered unacceptable. All of the acceptable materials were thixotropic semi-solids or viscous liquids that exhibited a significant viscosity reduction under shear. Some of the materials appeared to be coherent solids yet could readily be stirred by hand with a spatula using only a minimal amount of force.

Inorganic compounds yielding acceptable dispersions included:
Sodium p-toluenesulfonate
Calcium di-(p-toluenesulfonate)
Sodium Phenylphosphonate
Calcium Phenylphosphonate
Barium Acetate
Strontium Acetate
Zirconium Acetate
Manganous Acetate
Lead Acetate
Calcium Nitrate
Ferrous Nitrate
Ferric Nitrate
Zinc Nitrate
Sodium Silicate
Magnesium Chloride
Calcium Chloride
Manganous Chloride
Ferrous Chloride
Ferric Chloride
Cupric Chloride
Stannous Chloride
Bismuth Chloride Compounds which did not yield acceptable dispersions included:
Potassium p-toluenesulfonate
Potassium Phenylphosphonate
Potassium Acetate
Nickel(ous) Acetate
Cuprous Acetate
Cupric Acetate
Cadmium Acetate
Potassium Nitrate
Barium Nitrate
Nickel(ous) Nitrate
Magnesium Silicate
The chlorides of sodium, potassium & monovalent Copper
Calcium Fluoride It is believed that an effective stabilizer will interfere with the formation of strong bonds between the fluorine atoms on one molecule and tin atoms on adjacent molecules. This bond formation is believed responsible for the agglomeration which almost always occurs when a trialkyltin fluoride is dispersed into an organic solvent in the absence of one of the present inorganic compounds.

EXAMPLE 2

The effect of vaarious organic liquids or diluents on the stability of a dispersion containing 60% by weight of tri-n-butyltin fluoride, 5% of calcium carbonate and 35% of the organic liquid was determined by preparing a dispersion as described in the preceding example. Those dispersions which could be classified as viscous liquids or coherent semi-solids following the initial milling operation were stored for one week under ambient conditions and then examined to determine whether the original thixotropic character had been retained.

The organic liquids evaluated included a mixture of aromatic hydrocarbons available as Solvesso ® 150 from the Exxon Company and typically having a flash point from 145° to 150° F. (63° to 65° C.), VM&P naphtha [a mixture of aliphatic hydrocarbons typically having a flash point of 6.7° C. (tag closed cup) and a boiling range from 118° to 139° C.]; mineral spirits [a mixture of aliphatic hydrocarbons typically having a flash point of 42.2° C. (tag closed cup) and a boiling range from 160° to 196° C.]; ethyl benzene, amyl acetate, a mixture (A) containing 33.3% of VM&P naptha, 28.9% cyclohexane and 37.8% amyl acetate and a second mixture (B) containing 34.2% mineral spirits, 4.4% Solvesso ® 150, 12.2% ethyl benzene and 49.2% amyl acetate.

Also included in the evaluation were cyclohexane, xylene, 2-butanone, n-butyl acetate, isobutyl acetate, n-butanol, ethylene glycol, n-propanol, octanol, Cellosolve ® acetate (ethylene glycol monomethyl ether monoacetate) and toluene. Of the solvents evaluated, the two mixtures (A&B), VM&P naphtha, Solvesso ® 150, mineral spirits, xylene, n-butanol and octanol produced acceptable dispersions. Dispersions prepared using the other solvents hardened during the one week storage period or were two stiff and gum-like for use in a paint formulation.

EXAMPLE 3

A dispersion containing 60% by weight of tri-n-butyltin fluoride (TBTF) prepared as described in the preceding Example 1 using calcium chloride as the stabilizer, can be incorporated into a conventional paint formulation of the following composition:

|  | Parts |
| --- | --- |
| Titanium dioxide | 15.12 |
| Talc (magnesium silicate) | 11.22 |
| Zinc oxide | 7.08 |
| A vinyl chloride - vinyl acetate copolymer (VAGH) | 11.16 |
| Rosin | 3.73 |
| 2-butanone | 20.31 |
| Xylene | 18.84 |
| Bentonite clay | 0.51 |
| Methanol (95%) | 0.15 |
| TBTF[1] dispersion | As Required |

[1] tri-n-butyltin fluoride

The solvent employed to prepare the dispersions is a mixture containing 64% special naphthalite, 12% ethyl benzene, 9% n-butyl acetate, 5% isobutyl acetate and 10% n-butanol. Special naphthalite is described in the preceding Example 1.

The amount of tri-n-butyltin fluoride dispersion employed is equivalent to 12% by weight of the compound in the formulation. The dispersion was blended together with the other components of the formulation to achieve a homogeneous mixture.

The paint can be evaluated using a Hegman N.S. gauge to determine "fineness" of the grind. A 0.003 inch (0.0076 cm)-thick film is applied to a metal surface using a draw-down blade and the texture of the resultant film is evaluated using the following scale:
1. Rough surface easily detected by rubbing a hand over the surface of the coating
2. 10–20 observable lumps uniformly distributed on paint surface
3. Several lumps visible
4. Smooth The data from a typical paint evaluation are recorded in the following table. A Hegman fineness of 4 or 5 is considered acceptable.

| % CaCl₂ | Hegman Grind No. | Film Rating |
|---------|------------------|-------------|
| 10      | —                | 4           |
| 5       | —                | 4           |
| 2.5     | 4                | 4           |
| 1       | 4–5              | 3–4         |
| 0.5     | 4–5              | 1–2         |

The film prepared using a dispersion containing 0.5% by weight of calcium chloride and 60% tri-n-butyltin fluoride may be too rough in texture to be considered acceptable, however, this level of calcium chloride would be sufficient to stabilize dispersions containing less than 60% of the trialkyltin compound, for example about 50% by weight.

EXAMPLE 4

A typical red formulation suitable for use with the present dispersed form of tri-n-butyltin fluoride can be prepared using the following procedure:

| | |
|---|---|
| 1. Combine the following ingredients using a high speed stirrer to obtain a uniform dispersion: | |
| Rosin (70% by weight in xylene) | 4.89 parts |
| A mixture containing bentonite clay | 0.47 part |
| and methanol | 0.14 part |
| 2. Combine the mixture of (1) with cyclohexane | 12.00 parts |
| 3. Add the pigments | |
| Red iron oxide | 13.90 parts |
| Talc | 10.30 parts |
| Zinc oxide | 6.05 parts |
| 4. Add the film-forming polymer vinyl chloride/partially hydrolyzed vinyl acetate copolymer (available as VAGH from Union Carbide Corporation) as a 3% by weight solution in a 2-butanone-xylene mixture. | 34.13 parts |
| 5. Add a dispersed form of tri-n-butyltin fluoride as described in the preceding Example 1. | 17.65 parts |
| 6. Stir the mixture at high speed until the composition exhibits a fineness of 4 to 5 on the Hegman N.S. scale. | |

EXAMPLE 5

A dispersion containing 50% by weight of TBTF prepared as described in the preceding Example 1 using calcium chloride as the stabilizer can be incorporated into a conventional paint formulation wherein the film-forming component is a chlorinated rubber.

| INGREDIENT | PARTS |
|---|---|
| Red iron oxide | 17.24 |
| Zinc oxide | 8.09 |
| Talc (magnesium silicate) | 7.30 |
| Bentonite Clay¹ | 0.59 |
| Methanol | 0.18 |
| Chlorinated natural rubber² | 8.9 |
| Rosin | 8.9 |
| Xylene | 21.9 |
| TBTF dispersion | 26.9 |
| | 100.00 |

Notes:
[1]Bentone® 27, supplied by NL Industries.
[2]64–65% by weight of chlorine, viscosity = 17–25 cps, measured using a 20% by weight solution in toluene at 25° C.

The paint was prepared using the following procedure

1. Combine bentonite clay and methanol, mix thoroughly and combine with rosin; mix until homogeneous;
2. Add solvent (xylene) with the pigments to achieve the desired viscosity during dispersion;
3. Charge the pigments in order indicated and disperse to a 5 grind on the Hegman N.S. Scale:
   Red Iron Oxide: 17.24
   Zinc Oxide: 8.09
   Talc: 7.03;
4. Charge the chlorinated rubber slowly with agitation until dissolved; and
5. Add the TBTF dispersion and mix to achieve a 4–5 grind on the Hegman N.S. Scale.

What is claimed is:

1. A stable thixotropic dispersion, said dispersion consisting essentially of:
   (a) from 40 to 70% by weight of a trialkyltin fluoride of the formula $R_3SnF$ wherein R is alkyl containing from 2 to 12 carbon atoms;
   (b) from 20 to 60% by weight of at least one organic liquid having a kauri butanol value of 96 or less and selected from the group consisting of alcohols containing from 4 to 12 carbon atoms, aliphatic hydrocarbons containing from 5 to 12 carbon atoms and aromatic hydrocarbons;
   (c) from 0.5 to 10% by weight of a compound selected from the group consisting of:
      (1) the lithium and sodium salts of p-toluenesulfonic acid and phenylphosphonic acid,
      (2) nitric acid salts of calcium, magnesium, sodium, lithium, iron and zinc,
      (3) salts of p-toluenesulfonic or phenylphosphonic acid and an element selected from the group consisting of magnesium, calcium, strontium and barium,
      (4) the chlorides of metallic elements selected from the group consisting of divalent tin, divalent copper, silver, gold and the elements in groups II-A, II-B, IV-B, V-A, VI-B, VII-B and VIII of the periodic table and
      (5) carboxylic acid salts of lead, manganese(ous), zirconium, barium and strontium, wherein said carboxylic acid is selected from the group consisting of acetic, propionic, butyric, hexoic, heptanoic, cyclohexanecarboxylic and benzoic acids.

2. A stable dispersion according to claim 1 wherein R contains from 3 to 6 carbon atoms.

3. A stable composition according to claim 2 wherein R is butyl.

4. A stable dispersion according to claim 1 wherein said liquid organic medium is a mixture containing two aliphatic hydrocarbons.

5. A stable dispersion according to claim 1 wherein said organic liquid is xylene.

6. A coating composition for inhibiting the attachment and growth of fouling organisms, said composition consisting essentially of from 1.0 to 20.0% by weight of the trialkyltin fluoride containing dispersion as described in claim 1, from 10 to 50% by weight of at least one pigment, from 10 to 50% by weight of at least one film-forming material selected from the group consisting of vinyl chloride homopolymers and copolymers, rosin and chlorinated synthetic rubbers, from 20 to 60% by weight of at least one organic solvent and from 0 to 5% by weight of a bentonite clay.

7. A composition according to claim 6 wherein the trialkyltin fluoride is tri-n-butyltin flouride.

8. A composition according to claim 6 wherein the pigment is a mixture of titanium dioxide, zinc oxide and magnesium silicate.

* * * * *